(12) United States Patent
Lub et al.

(10) Patent No.: US 7,261,836 B2
(45) Date of Patent: Aug. 28, 2007

(54) CHIRAL DOPANT WITH PHENYLETHANEDIOL FUNCTIONALITY

(75) Inventors: Johan Lub, Eindhoven (NL); Rene Theodorus Wegh, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 199 days.

(21) Appl. No.: 10/519,604

(22) PCT Filed: Jun. 13, 2003

(86) PCT No.: PCT/IB03/02927
§ 371 (c)(1),
(2), (4) Date: Dec. 27, 2004

(87) PCT Pub. No.: WO2004/002935
PCT Pub. Date: Jan. 8, 2004

(65) Prior Publication Data
US 2006/0022167 A1 Feb. 2, 2006

(30) Foreign Application Priority Data
Jun. 28, 2002 (EP) .................................. 02077561

(51) Int. Cl.
C09K 19/36 (2006.01)
C09K 19/20 (2006.01)
C07C 69/73 (2006.01)
(52) U.S. Cl. ............................. 252/299.7; 252/299.67; 428/1.1; 428/1.3; 560/181; 560/183
(58) Field of Classification Search ........... 252/299.67, 252/299.7; 428/1.1, 1.3; 560/181, 183
See application file for complete search history.

(56) References Cited

U.S. PATENT DOCUMENTS 6,849,203 B2 * 2/2005 Farrand et al. ......... 252/299.01
6,953,611 B2 * 10/2005 Hammond-Smith et al. . 428/1.3
2004/0026660 A1 * 2/2004 Vaughan-Spickers et al. .... 252/299.01

FOREIGN PATENT DOCUMENTS

WO WO 02/40614 * 5/2002

OTHER PUBLICATIONS

J. A. Rego et al: "Synthesis of Chrial Networks for Polymer Stabilized Cholesteric Texture (PSCT) Displays" Apr. 1997.

* cited by examiner

*Primary Examiner*—Shean C Wu

(57) ABSTRACT

The invention pertains to a phenylethanediol derivative having at least one polymerizable group, characterized in that the phenylethanediol derivative further comprises at least one photo-convertible group for adjusting the helical twisting power of the phenylethanediol derivative. According to a preferred embodiment the phenylethanediol has the formula

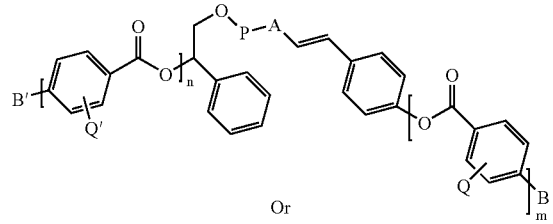

Or

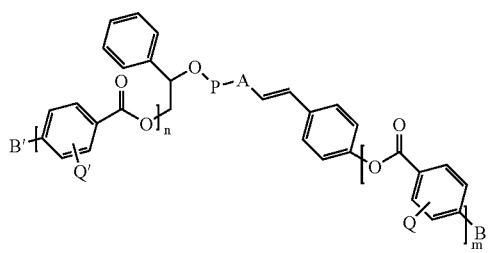

wherein
A stands for a bond or a p-phenylene group;
B and B' are independently $(O)_p$—$C_oH_{2o}$—O—CO—CR'=$CH_2$, o being 2-12, p being 0 or 1, and R' being H or $CH_3$;
P stands for a $CH_2$ or a C=O group;
Q and Q' are independently selected from H, C1-C3 alkyl, C1-C3 alkoxy, halogen, and CN;
n is an integer from 1 to 3; and
m is an integer from 0 to 2; and:

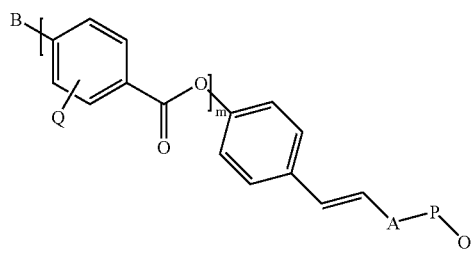

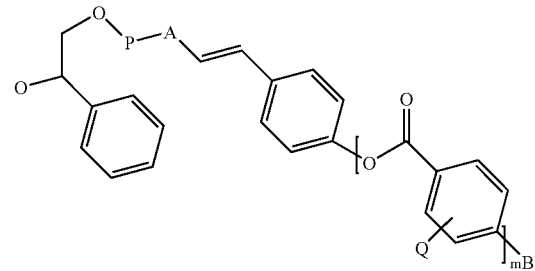

Figure 1A:
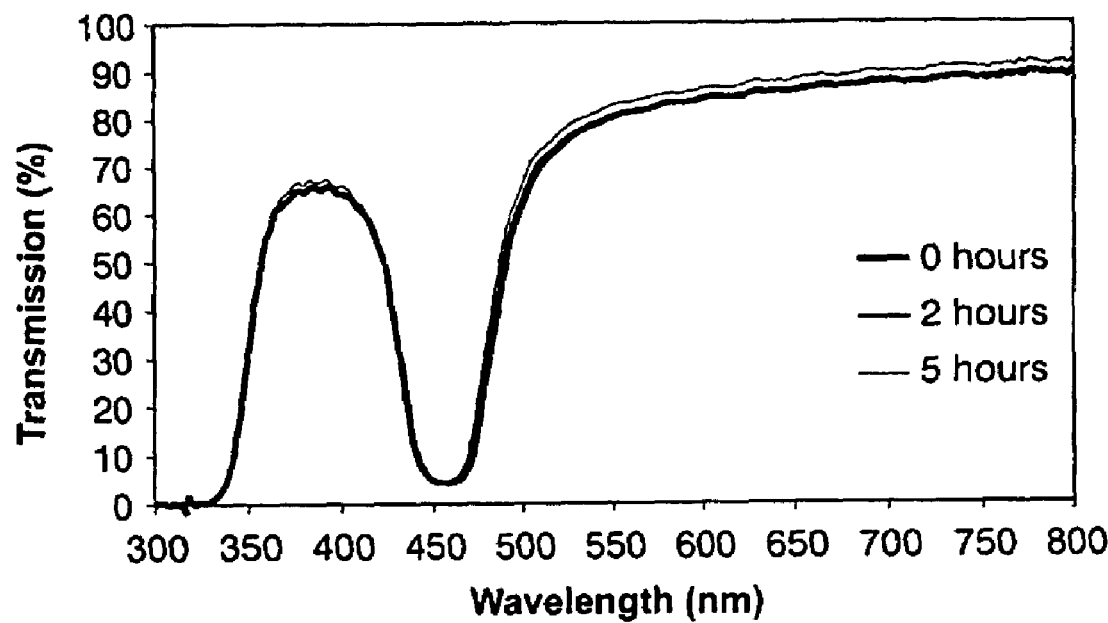

wherein
A stands for a bond or a p-phenylene group;
B is $(O)_p$—$C_oH_{2o}$—O—CO—CR'=$CH_2$, o being 2-12, p is 1, and R' being H or $CH_3$;
P stands for a $CH_2$ or a C=O group;
Q is selected from H, C1-C3 alkyl, C1-C3 alkoxy, halogen, and CN; and
m is an integer from 0 to 2.

9 Claims, 1 Drawing Sheet

CHIRAL DOPANT WITH PHENYLETHANEDIOL FUNCTIONALITY

The invention pertains to a phenylethanediol derivative preferably having at least one polymerizable group, to a method for the preparation thereof, to a cholesteric composition and an optical element comprising said phenylethanediol derivative, and to the use of the phenylethanediol derivative in optical elements.

Chiral derivatives having a polymerizable group are known in the art. For instance, in WO 98/00428 chiral dopants were disclosed comprising an isosorbide moiety and ester groups. In this reference it is explained that these chiral dopants are used to induce or enhance the helical twist of the molecules of a liquid crystalline medium, which can be used to make cholesteric color filters (CCF's).

Other derivatives having a polymerizable group are known from WO 99/64383, disclosing optically active butane-1,2,3,4-tetraol derivatives for use in cholesteric filters. These derivatives can be polymerized and can also be used as chiral dopant in cholesteric networks.

All these prior art derivatives usually have high helical twisting power (HTP) values, but the pitch of the helix of the liquid crystalline molecules can only be adjusted by varying the concentration of the dopant. It would be a substantial advantage when at the same concentration of the chiral dopant different pitches of the helix could be attained. In WO 00/34808 other chiral dopants have been disclosed, i.e. menthone derivatives having both polymerizable and photo-isomerizable groups, and various methods of providing a variation in the pitch are discussed. These chiral dopants can be used in CCF's for reflective and transmissive LCD's (liquid crystal displays). Such filters are made by applying a solution of a mixture of nematic compounds, for instance diacrylates, a photosensitive chiral compound, and a photo-initiator onto a substrate by using a coating technique such as spin coating. By irradiation through a mask color formation is performed, after which the color is fixed by photo-polymerization and the color film is obtained as a stable crosslinked film. The pitch p of the molecular helix depends on the concentration of the chiral dopant and is inversely proportional to a factor that is called the helical twisting power (HTP). The pitch of the helix and the direction of the helix (right or left handed helix) determine the wavelength at which light is reflected from the cholesteric liquid crystals and whether the reflected light is polarized right or left handed. Its relatively high HTP values allow the use of low concentrations of chiral dopant, which is important since these dopants are expensive and difficult to make. It is further explained that a short pitch is sometimes demanded, whereas for other applications a long pitch is required. This can be realized by adapting the concentration of the chiral dopant. Moreover, the pitch can be varied as a function of position in the film by the introduction of a photo-isomerizable chiral compound, preferably a chiral acrylate. The degree of conversion is determined by the radiation intensity, and the pitch of the cholesterically ordered material is determined by the extent of conversion of the photo-isomerizable compound. A specific chiral dopant that satisfies these conditions was disclosed to be a menthone derivative, which is a benzene derivative with an ether group separated by a spacer from an acrylic moiety and at the para position having an ester group comprising a photo-isomerizable cyclohexylidene moiety. Although the principle as outlined in WO 00/34808 appears to be a substantial improvement to the art, the photo-isomerizable menthone derivative as used is far from ideal since it has only limited thermal stability. Since heating steps are necessary to make LCD's (liquid crystalline displays) color filters comprising these menthone derivatives lose their optical performance. Furthermore, it is desirable to improve the alignment capability of the prior art menthone derivatives. It is further desired to find optical derivatives, which can be made of cheap starting materials. Preferably, each of the enantiomers is commercially available.

It is therefore an object of the present invention to provide a chiral dopant with relatively high HTP values, and improved thermal stability and alignment capability, which can be prepared from inexpensive commercially available materials. It has now been surprisingly found that phenylethanediol derivatives can be provided with photo-convertible groups to give derivatives with extremely good thermal stability, sufficiently high HTP values, and excellent alignment capability. These derivatives can be prepared starting from ethyl mandelate, of which both enantiomers are easily available. The invention therefore relates to phenylethanediol derivatives preferably having at least one polymerizable group, characterized in that the phenylethanediol derivative further comprises at least one photo-convertible group suitable for adjusting the helical twisting power of the phenylethanediol derivative.

Persons skilled in the art will appreciate that in general any two chiral dopants and therefore also chiral dopants comprising, in accordance with the invention, a phenylethane diol, having a different chemical structures will have a different helical-twisting power. Furthermore, obviously, the helical-twisting power of a compound which is not a chiral dopant is different from a chiral dopant, the former being characterized by the absence of helical twisting power. Accordingly, persons skilled in the art will appreciate that any photochemical reaction known in the art as such can in principle be used as a basis to provide suitable embodiments of photo-convertible groups. In particular, photo-convertible groups may be used which upon irradiation become cyclic or, just the opposite, ring-open, or different types of rearrangements. Alternatively, photo-cleavable groups may be used such as those disclosed in U.S. Pat. No. 5,668,614. Preferably however, the photo-convertible group is a photo-isomerizable group. Suitable photo-isomerizable groups comprise an olefinic moiety that can undergo E-Z isomerization upon irradiation. Examples of such groups are derived from styrene- and stilbene-like compounds.

The phenylethanediol derivatives of the invention preferably further comprise a polymerizable group. Suitable polymerizable groups, in particular photo-polymerizable groups, include but are not limited to epoxides, vinylethers, oxetanes, cinnamates, and thiolenes. A preferred (photo)-polymerizable group is the (meth)acrylate group. The phenylethanediol molecule contains two hydroxy groups, at least one, but preferably both, thereof being esterified or etherified with a substituent. The substituents comprise the photo-convertible and preferably photo-polymerizable groups. The photo-convertible and photo-polymerizable groups may be contained in the same or in different substituents. It also may be that the different substituents comprise the same or different photo-convertible and/or photo-polymerizable groups, or that the photo-convertible and photo-polymerizable groups are contained in only one of the ester or ether substituents, whereas the other hydroxy group of the phenylethanediol is a free hydroxy group or is esterified or etherified with a substituent that does not comprise a photo-convertible and/or photo-polymerizable group.

The phenylethanediol group is a group which, when esterified or etherified, enables or at least does not preclude the phenylethanediol derivative so obtained to be or become a chiral dopant, that is a compound which when added to a non-optically active liquid crystal composition, such as a nematic liquid crystal composition, changes that composition into an optically active composition, such as a chiral nematic composition (cholesteric composition) or modifies the optical properties of an optically active liquid crystal composition when added to such optically active liquid crystal composition. To enable the formation of an optically active liquid crystal composition, a chiral dopant molecule generally has a chiral center, typically a chiral carbon atom, and a shape which is similar to the molecules of the liquid crystal composition to which the chiral dopant is to be added. In particular, in order to obtain suitable phenylethanediol derivative in accordance with the invention the phenylethanediol derivative is esterified or etherified with mesogenic groups or parts of the mesogenic groups. Such mesogenic groups or parts of such mesogenic are well known in the art. More specific phenylethanediol derivatives in accordance with the invention may include but are limited to those comprising -(T4-L4)$_{q1}$-T2-L2-PED-L1-T1-(L3-T3)$_{q2}$- wherein PED is the esterified or etherified phenylethanediol group, L1 and L2, the same or different at each occurrence, a single bond, carbonyl, $CH_2$, —$CH_2CH_2$—, —CH=CH—, ethynylene, —$OCH_2$—, L3 and L4, the same or different at each occurrence, L1, L2, thionyl, oxygen, sulfur carboxyl, —C=N—, —N=N—, amide, T1, T2, T3, T4, the same or different at each occurrence, a substituted or unsubstituted phenylene, naphthalene, cyclohexylene, or other C1-C15 aromatic or saturated ring wherein 1 to 6 carbon atoms may be replaced with N, O or S, and q1 and q2, the same or different, 0 to 6. Preferred phenylethanediol derivatives were found to have the formula

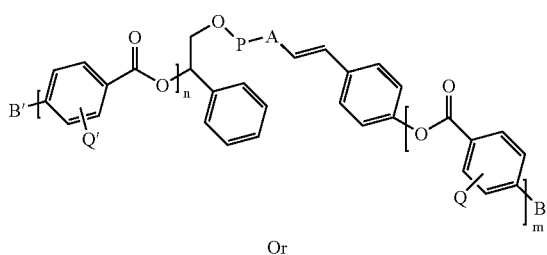

Or

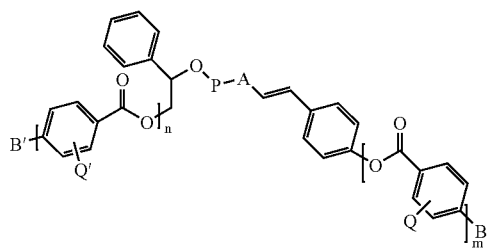

wherein

A stands for a bond or a p-phenylene group;

B and B' are independently (O)$_p$—$C_oH_{2o}$—O—CO—CR'=$CH_2$, o being 2-12, p being 0 or 1, and R' being H or $CH_3$;

P stands for a $CH_2$ or a C=O group;

Q and Q' are independently selected from H, C1-C3 alkyl, C1-C3 alkoxy, halogen, and CN;

n is an integer from 1 to 3; and m is an integer from 0 to 2.

The term C1-C3 alkyl means an alkyl group with 1 to 3 carbon atoms, i.e. methyl, ethyl, propyl, and isopropyl. The term C1-C3 alkoxy means an alkoxy group with these alkyl groups. The term halogen means a halogen atom, such as fluorine, chlorine, bromine, and iodine.

In another preferred embodiment the phenylethanediol has the formula

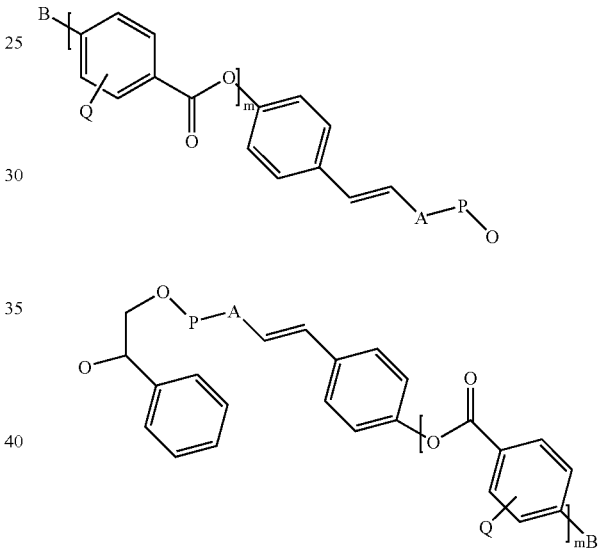

wherein

A stands for a bond or a p-phenylene group;

B is (O)$_p$—$C_oH_{2o}$—O—CO—CR'=$CH_2$, o being 2-12, p is 1, and R' being H or $CH_3$;

P stands for a $CH_2$ or a C=O group;

Q is selected from H, C1-C3 alkyl, C1-C3 alkoxy, halogen, and CN; and m is an integer from 0 to 2.

Although from a synthetic point of view it is preferred that in these compounds both 1- and 2-hydroxy substituents are the same, it is also possible to use compounds wherein the two substituents are different, i.e. wherein A, B, P, Q, o, p, and/or m are differently selected for the two substituents. When both substituents are the same, the synthesis can be simplified by using a direct etherification or esterification of phenylethanediol, without first selectively protecting the one of the hydroxy groups. Examples of phenylethanediol derivatives according to this invention are:

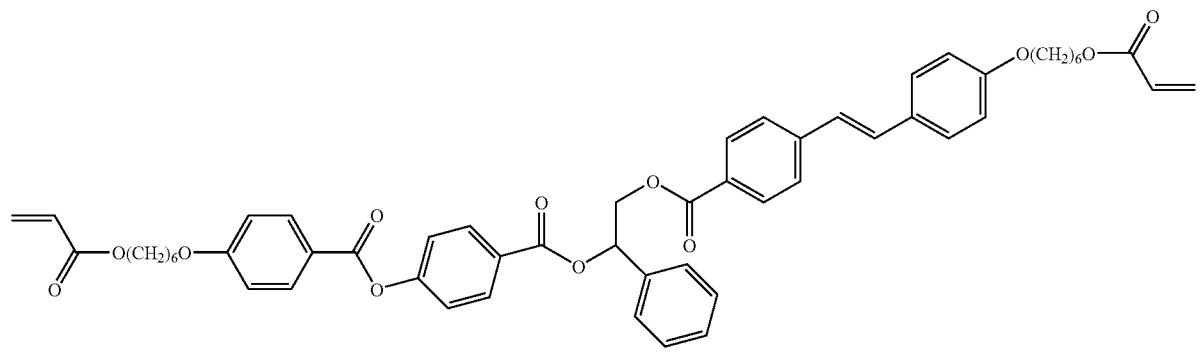

(phenylethanediol 1)

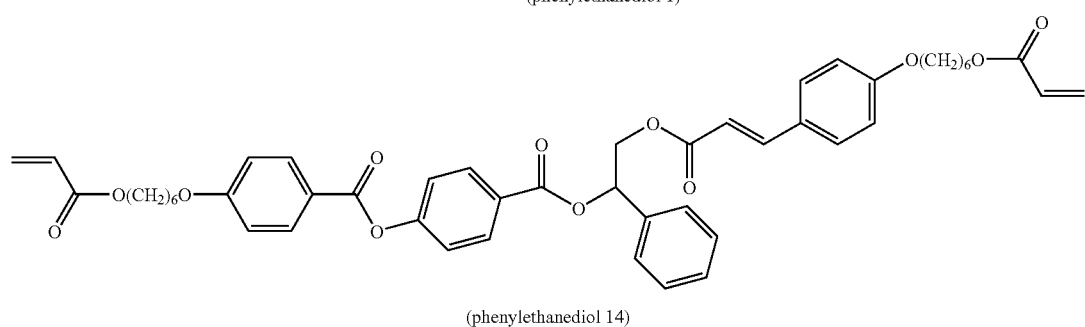

(phenylethanediol 14)

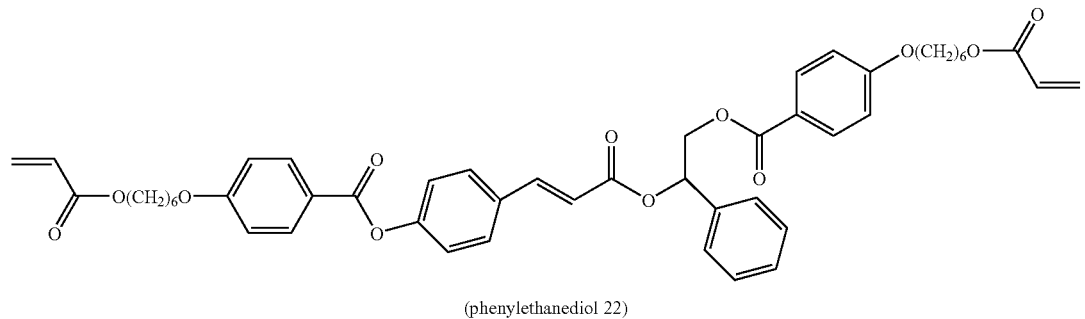

(phenylethanediol 22)

The phenylethanediol derivatives according to the invention may be used as a cholesteric composition mixed with other chiral compounds, for instance such as with a non-isomerizable phenylethanediol derivative (phenylethanediol D) of the formula:

The phenylethanediol derivatives of the invention can be prepared from L-ethyl or D-ethyl mandelate in which the hydroxy group is protected with a temporarily protective group, such as an ether group. The ethyl ester group of the protected ethyl mandelate can then be reduced in a common

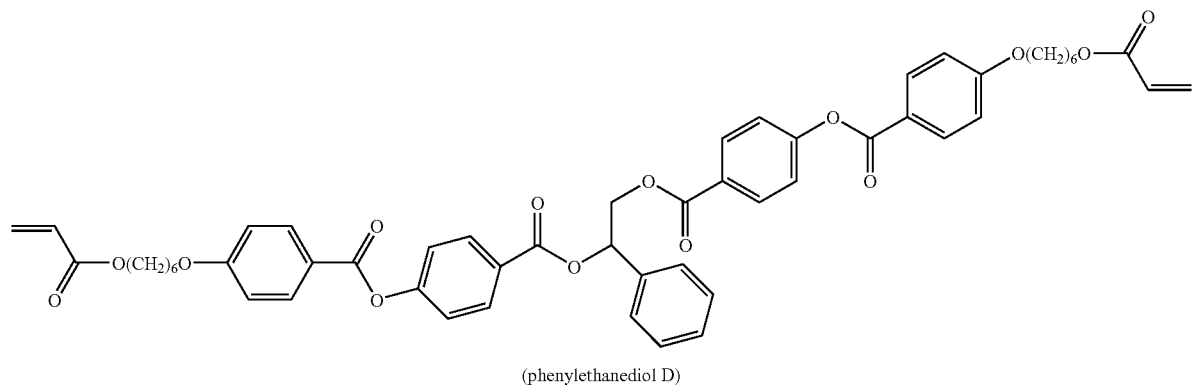

(phenylethanediol D)

manner known in the art, such as reduction with lithium aluminum hydride, sodium boronhydride, and the like. The present modified synthesis enables to make phenylethanediols that selectively have different substituents at their 1- and 2-hydroxy groups. The present method therefore comprises a) synthesizing a 1-hydroxy ether-protected phenylethanediol, b) followed by etherification or esterification of the 2-hydroxy group of the 1-hydroxy ether-protected phenylethanediol with an alcohol (or derivative thereof) or acid, respectively, optionally comprising polymerizable and/or photo-convertible groups, c) then cleaving the ether-protective group to obtain a phenylethanediol derivative with a free 1-hydroxy group, and optionally d) esterification of the free 1-hydroxy group with an acid, which optionally comprises one or more polymerizable and/or photo-convertible groups.

This method has the advantage that no separation is necessary of the 1-hydroxy ether-protected phenylethanediol from the 2-hydroxy ether-protected, 1,2-dihydroxy ether-protected, and unprotected phenylethanediols. The ether-protecting group can be any common group that is known in the art for the protection of hydroxy groups through an ether linkage. Preferred ether-protective groups are the THP (tetrahydropyranyl) ether and the ethoxyethyl ether groups that are formed when a hydroxy group is reacted with 3,4-dihydro-2H-pyran and ethylvinylether, respectively, and which can easily be cleaved under mild acidic conditions to release the hydroxy group.

The alignment of the CCF based on these phenylethanediol derivatives and therefore the reflection intensity is significantly improved. Most importantly, the thermal stability is much higher than that of the menthone derivative based CCF's. Upon irradiation photo-conversion, particularly photo-isomerization occurs leading to an HTP change that is sufficient to change the color from blue to red. The concentration of the chiral photo-convertible compounds is chosen in such a way by making mixtures with non-chiral compounds, to obtain a blue reflecting layer before irradiation. A red layer is then obtained after a certain period of irradiation. If both a photo-convertible and a non-photo-convertible chiral dopant are used, e.g. phenylethanediols 1 or 14 or 22 together with D, and the concentrations are chosen properly, a layer can be obtained that reflects blue before irradiation and red in the photostationary state. This means that only the formation of a green color depends on the total UV dose, thus making the manufacture of a mask for pixelated irradiation very simple. This makes the phenylethanediol derivatives suitable for use in optical elements, preferably in optical color filters.

The invention is further illustrated by the following non-restrictive examples.

EXAMPLE 1

Synthesis of (E)-(R)-4-(2-phenyl-2-(4-(6-acryloyloxyhexyloxy)benzoyloxyethyloxy)methyl 4'-hexyloxy stilbene (1)

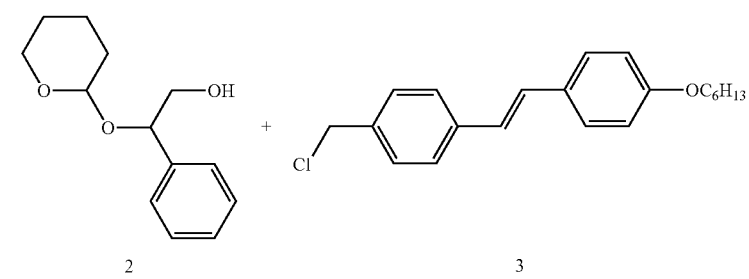

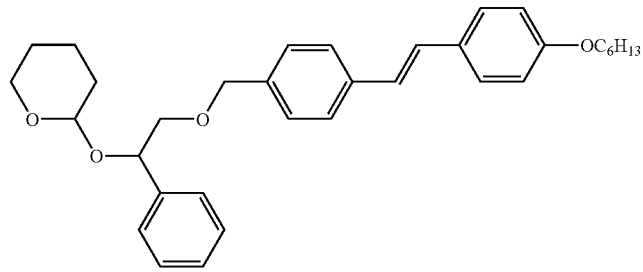

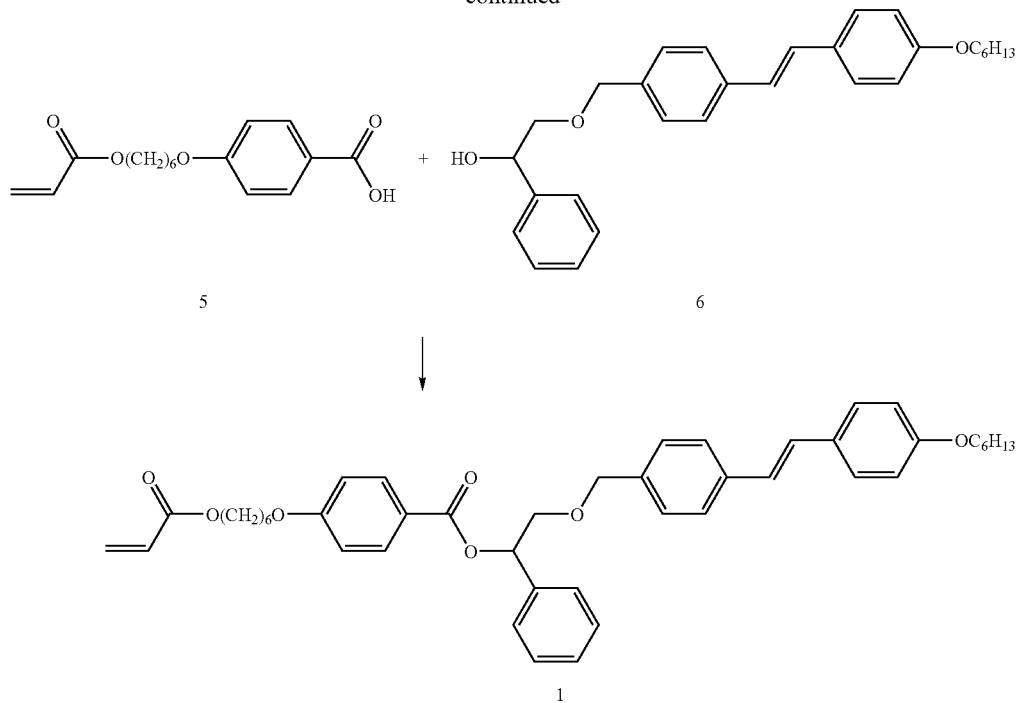

A: (R)-2-(2-{4-[2-(4-Hexyloxy-phenyl)-vinyl]-benzyloxy}-1-phenyl-ethoxy)-tetrahydro-pyran (4).

0.75 g (3.35 mmole) of (R)-2-Phenyl-2-(tetrahydro-pyran-2-yloxy)-ethanol (2) were added to a solution of 0.4 g (6.08 mmole) of powdered KOH (85%) in 6 ml of dimethylsulfoxide. After 10 min stirring 1 g (3 mmole) of (E)-4-chloromethyl-4'-hexyloxystilbene (3) was added in small portions. The reaction was stirred overnight at room temperature under $N_2$ atmosphere.

60 ml of water were added and the product was precipitated. The powder was filtered and washed with 25 ml of water and dried in air. 1.4 g of white-yellow powder was obtained.

B: (E)-(R)-4-(2-phenyl-2-hydroxyethyloxy)methyl 4'-hexyloxy stilbene (6).

1.4 g of (R)-2-(2-{4-[2-(4-Hexyloxy-phenyl)-vinyl]-benzyloxy}-1-phenyl-ethoxy)-tetrahydro-pyran (4) were dissolved in 30 ml of ethanol. Hydrochloric acid was added dropwise to obtain an acidic medium. Then the mixture was refluxed for 30 min. Upon cooling the product crystallized. The solid was filtered, washed with ethanol, and dried in a dessicator.

1 g of yellow powder was obtained (overall yield: 74.5%)

C: (E)-(R)-4-(2-phenyl-2-(4-(6-acryloyloxyhexyloxy)benzoyloxyethyloxy)methyl 4'-hexyloxy stilbene (1).

0.26 g of N,N'-dicyclohexyl carbodiimide (2.25 mmole) were added to a mixture of 0.035 g (0.225 mmole) of 4-N,N-dimethylaminopyridine, 1 g (2.25 mmole) of (E)-(R)-4-(2-phenyl-2-hydroxyethyloxy)methyl 4'-hexyloxy stilbene (6), 0.66 g (2.25 mmole) of 4-(6-acryloyloxyhexyloxy) benzoic acid (5) and 10 ml of dichloromethane, and stirred in an ice-water bath. After 30 min the ice-water bath was removed and the reaction was stirred overnight at room temperature. The mixture was filtered through a silica pad and evaporated. The remaining solid was crystallized twice from alcohol to obtain 0.7 g of the product (47%) as a yellowish powder with mp 87° C.

EXAMPLE 2

Synthesis of (E)-4-chloromethyl-4'-hexyloxystilbene (3)

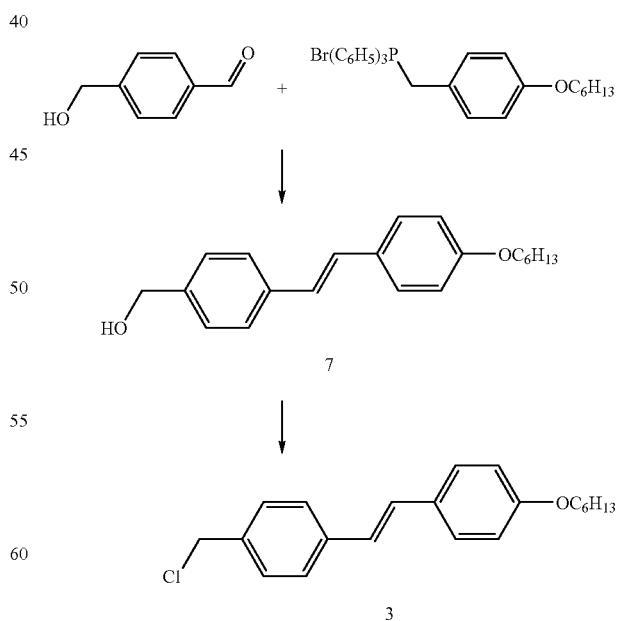

A: (E)-4-hydroxymethyl-4'-hexyloxystilbene (7).

115 mg (16.5 mmole) of Li were dissolved in 75 ml of ethanol under nitrogen atmosphere. Then 2.05 g (15 mmole)

of aldehyde 4-hydroxymethylbenzaldehyde were added and the mixture was cooled in an ice bath. Then 5.148 g (15 mmole) of (4-hexyloxy-benzyl)-triphenyl-phosphonium bromide were added. The mixture was stirred in the ice bath under nitrogen for 30 min, and then stirred at room temperature for 3 h. 2.5 ml of water were added and the precipitate was collected on a filter and washed with 10 ml of ethanol. After drying over silica in a dessicator 1.75 g of white powder was obtained. Yield: 37%.

B: (E)-4-chloromethyl-4'-hexyloxystilbene (3).

To a solution of 1.7 g (5.5 mmole) of (E)-4-hydroxymethyl-4'-hexyloxystilbene (7) in 12 ml of dichloromethane cooled in an ice bath under $N_2$ atmosphere were added dropwise 0.5 ml of thionylchloride in 3 ml of dichloromerthane. After 1.5 h 16 ml of water were added and the organic layer was separated. It was washed with 12 ml of brine, dried over $MgSO_4$ and the solvent was evaporated. A white solid was obtained which was recrystallized from 80 ml of a 1:1 mixture of hexane and ethanol. 1.1 g of white crystals were obtained (yield: 60%).

EXAMPLE 3

Synthesis of (R)-2-Phenyl-2-(tetrahydro-pyran-2-yloxy)-ethanol (2)

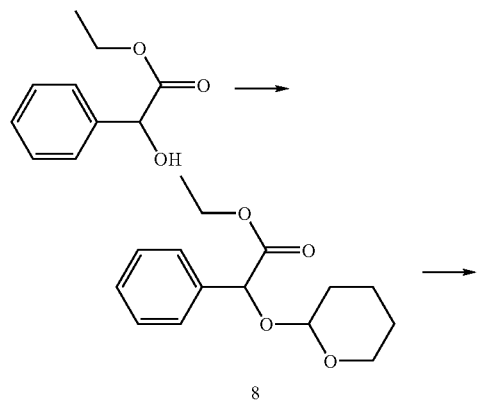

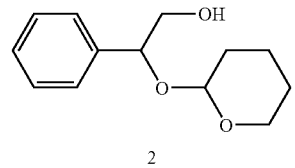

A: (R)-(−)-ethyl-2-phenyl-(tetrahydropyranyloxy)-acetate (8).

A solution of 10 g (55 mmole) of ethyl(R)-(−)-mandelate, 0.7 g (2.8 mmole) of pyridinium 4-toluenesulfonate and 7.6 ml (83.3 mmole) of 3,4-dihidro-2H-pyran in 50 ml of dichloromethane was stirred at room temperature for 24 h. The solution was extracted once with 25 ml of water and once with 25 ml of $NaHCO_3$ (5%). It was dried over magnesium sulfate and the solvent was evaporated to leave 14.28 g (97%) of a clear oil.

B: (R)-2-Phenyl-2-(tetrahydro-pyran-2-yloxy)-ethanol (2).

A solution of 4 g (15.1 mmole) of (R)-(−)-ethyl-2-phenyl-2-(tetrahydropyranyloxy)acetate (8) in 75 ml of dry ether was added dropwise to a stirred suspension of 1.72 g (45.3 mmole) of lithium aluminium hydride and 50 ml of ether at room temperature. After the addition was completed, the mixture was refluxed for additional 2 h, then cooled in an ice bath, and treated carefully subsequently with 1.72 ml of water, 1.72 ml of 15% sodium hydroxide, and 5.4 ml of water. After being stirred for additional 30 min, the mixture was filtered with suction, and the precipitate (aluminum salts) was washed with ether. The combined ethereal solution was dried over magnesium sulfate, and the solvent was evaporated to leave 3.3 g of a clear oil (97%).

EXAMPLE 4

Synthesis of (R)-4-(6-Acryloyloxy-hexyloxy)-cinnamic acid 2-[4-(4-(6-acryloyloxyhexyloxybenzoyloxy)benzoyloxy]-1-phenyl-ethyl ester (9)

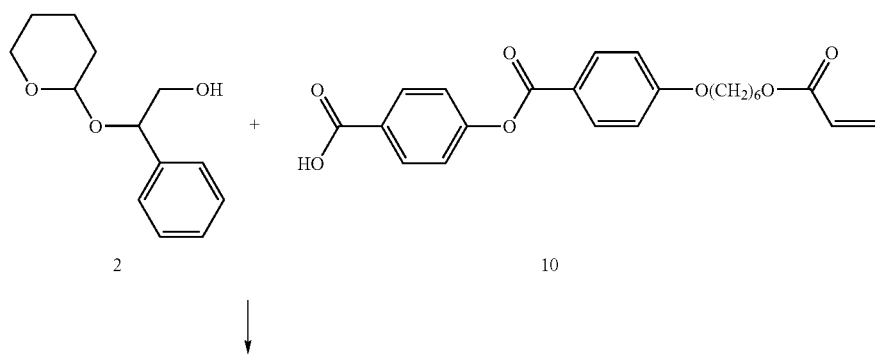

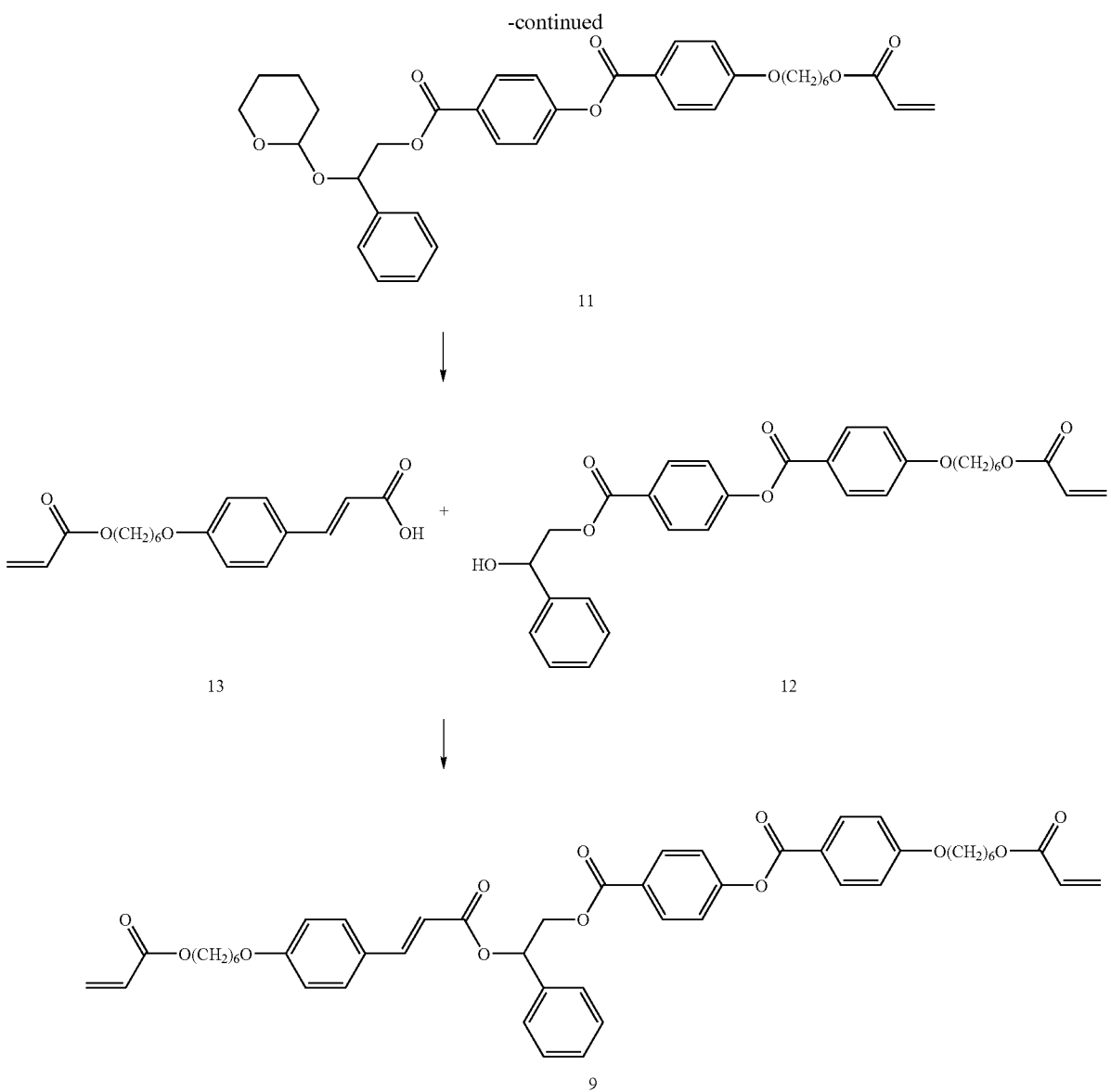

A: (R)-4-(4-(6-acryloyloxyhexyloxybenzoyloxy)benzoic acid 2-(tetrahydropyran-2-yloxy)-2-phenyl-ethyl ester (11).

A mixture of 2.22 g (0.01 mol) of (R)-2-Phenyl-2-(tetrahydro-pyran-2-yloxy)-ethanol (2), 4.12 g (0.01 mole) of 4-(4-(6-acryloyloxyhexyloxy)benzoyloxy)benzoic acid (13), 0.12 g (1 mmole) of 4-N,N-dimethylaminopyridine and 50 ml of dichloromethane was stirred under nitrogen atmosphere in an ice-water bath. Then 2.06 g of N,N'-dicyclohexyl carbodiimide were added. After 2.5 h the bath was removed. After 3 days the mixture was filtered over a silica pad and the solvent was evaporated to leave a clear oil that became a white solid upon standing.

B: (R)-4-(4-(6-acryloyloxyhexyloxybenzoyloxy)benzoic acid 2-hydroxy-2-phenyl-ethyl ester (12).

The crude (R)-4-(4-(6-acryloyloxyhexyloxybenzoyloxy) benzoic acid 2-(tetrahydropyran-2-yloxy)-2-phenyl-ethyl ester (11) was dissolved in 35 ml of ethanol and 0.25 g (1 mmole) of pyridinium 4-toluensulfonate and 40 mg of 4-methoxyphenol were added. The mixture was heated at 55° C. for 15 h. After cooling to 0° C. the product precipitated. 3.2 g of a white solid was obtained (60%).

C: (R)-4-(6-Acryloyloxy-hexyloxy)-cinnamic acid 2-[4-(4-(6-acryloyloxyhexyloxybenzoyloxy)benzoyloxy]-1-phenyl-ethyl ester (9).

A mixture of 3.2 g (6 mmole) of (R)-4-(4-(6-acryloyloxyhexyloxybenzoyloxy)benzoic acid 2-hydroxy-2-phenyl-ethyl ester(12), 1.91 g (6 mmole) of 4-(6-acryloyloxyhexyloxy)cinnamic acid (13), 0.073 g (0.6 mmole) of 4-N,N-dimethylaminopyridine and 40 ml of dichloromethane was stirred atmosphere in an ice-water bath. Then 1.3 g of N,N'-dicyclohexyl carbodiimide were added. After 2.5 h the bath was removed. The mixture was stirred overnight under and then filtered through a silica pad. The solvent was evaporated to leave clear oil that became a white waxy solid upon standing. The solid was washed twice with ethanol. 5.3 g of a white powder was obtained (68%) with mp 81° C.

EXAMPLE 5

Synthesis of (R)-4-(6-Acryloyloxy-hexyloxy)-cinnamic acid 2-[4-(4-(6-acryloyloxyhexyloxybenzoyloxy)benzoyloxy]-2-phenyl-ethyl ester (14)

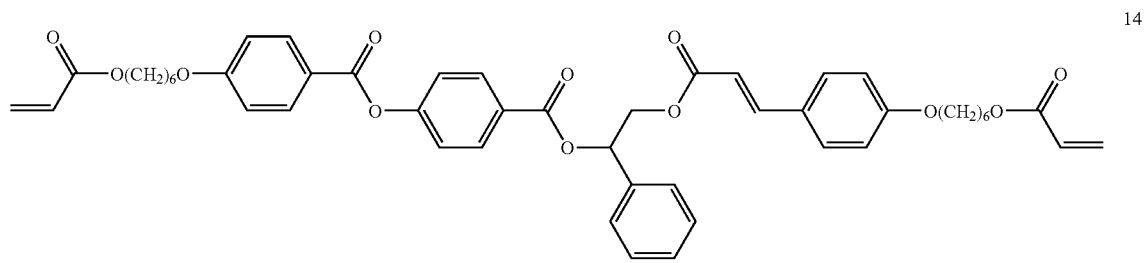

14

This compound was prepared in the same way as (R)-4-(6-Acryloyloxy-hexyloxy)-cinnamic acid 2-[4-(4-(6-acryloyloxyhexyloxybenzoyloxy)benzoyloxy]-1-phenyl-ethyl ester (9). In this reaction sequence compound 10 was changed for 13. Mp 53° C.

EXAMPLE 6

Synthesis of 4-(4-(6-acryloyloxyhexyloxy)benzoyloxy)benzoic acid (10)

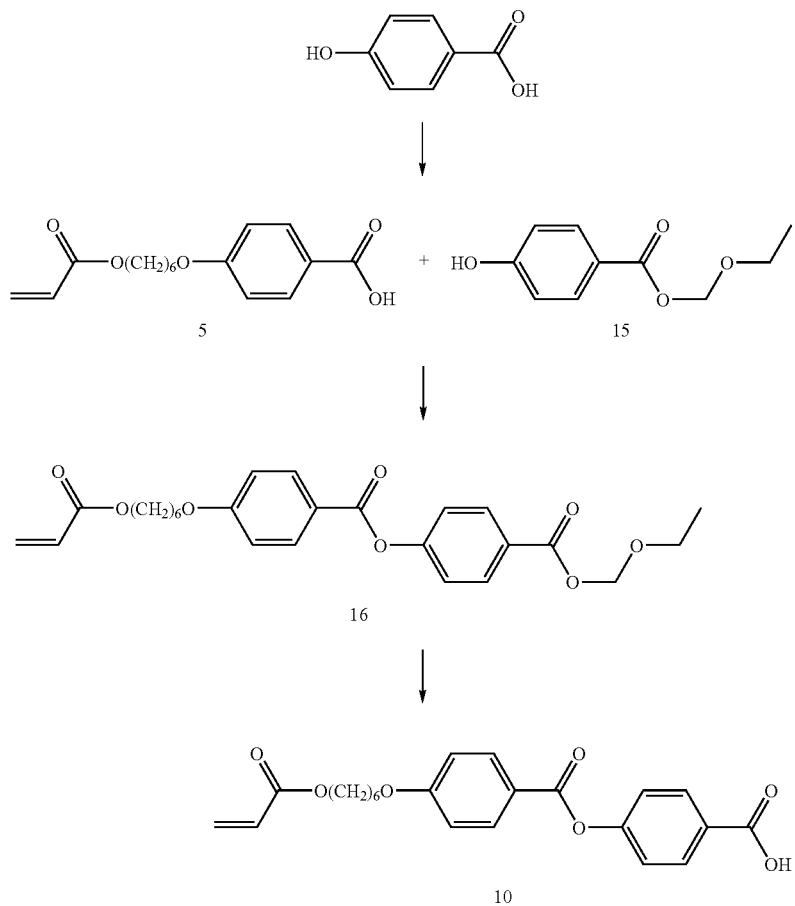

A: 4-Hydroxy-benzoic acid ethoxymethyl ester (15).

36.7 ml (0.26 mole) of triethylamine were added under $N_2$ atmosphere to a solution of 36.1 g (0.26 mole) of 4-hydroxybenzoic acid in 200 ml of dichloromethane. The mixture was cooled in an ice-water bath, and 24.5 ml (0.26 mole) of chloromethyl ethyl ether in 100 ml of dichloromethane were added dropwise.

After stirring for 1.5 h, the mixture was washed once with 150 ml of water then with 13 ml of hydrochloric acid (2.4 M) in 150 ml of water. Finally the solution was washed with 150 ml of saturated solution of $NaHCO_3$ and filtered through a filter paper. The solvent was evaporated. The oil was dissolved in 500 ml of diethyl ether and washed once with 250 ml of water, once with 250 ml of saturated solution of $NaHCO_3$, and finally with 250 ml of brine. The organic layer was dried over $MgSO_4$, and the solvent was evaporated. 42.2 g of a clear oil (77%) were obtained, after few minutes it crystallized as white crystals.

B: ethoxymethyl 4-(4-(6-acryloyloxyhexyloxy)benzoyloxy) benzoate (16).

To a solution of 42.2 g (0.20 mole) of 4-Hydroxy-benzoic acid ethoxymethyl ester (15) in 520 ml of dichloromethane were added 58.3 g (0.2 mole) of 4-(6-acryloyloxy-hexyloxy)-benzoic acid (5) and 2.4 g (0.02 mole) of 4-N,N-dimethylaminopyridine under $N_2$ atmosphere. The mixture was cooled in an ice-water bath. After few minutes 41.15 g (0.2 mole) of N,N-dicyclohexyl carbodiimide were added. Then the ice-water bath was removed. It was stirred at room temperature under $N_2$ for one night. Then the mixture was filtered and extracted twice with 300 ml of hydrochloric acid (2.4 M).

The organic layer was passed through a filter paper and the solvent was evaporated to leave 98.5 g of a clear oil (100%).

C: 4-(4-(6-acryloyloxyhexyloxy)benzoyloxy)benzoic acid (10).

98.5 g (0.2 mole) of ethoxymethyl 4-(4-(6-acryloyloxy-hexyloxy)bezoyloxy)benzoate (16) were dissolved in 400 ml of ethanol and 5 g (0.02 mole) of pyridinium 4-toluensulfonate and 20 mg of 4-methoxyphenol were added. The mixture was heated at 60° C. for 15 h. After cooling down at room temperature the product crystallized. It was collected, washed with 300 ml of ethanol, and dried in a desiccator 55.3 g of a white powder (67%) were obtained.

EXAMPLE 7

Synthesis of 4-(6-acryloyloxyhexyloxy)cinnamic acid (13)

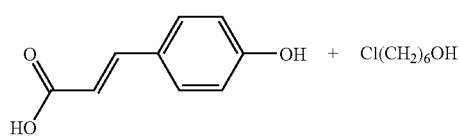

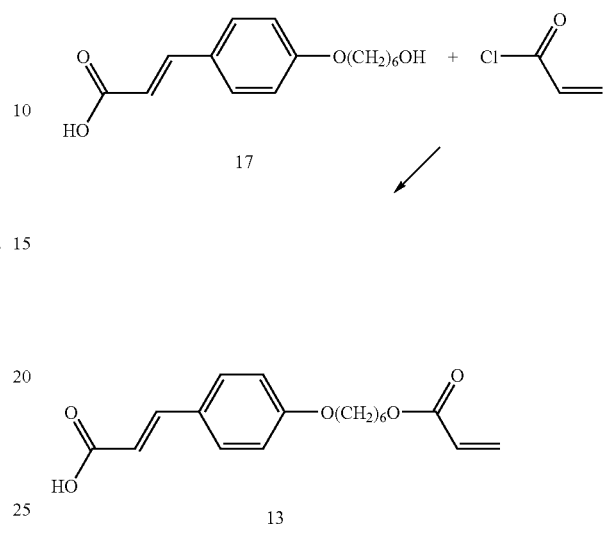

A: 4-(6-hydroxyhexyloxy)cinnamic acid (17).

To a mixture of 24.62 g (0.15 mole) 4-hydroxycinnamic acid and 0.29 g (1.65 mmole) of potassium iodide in 60 ml of ethanol was added under nitrogen atmosphere in 10 min a solution of 20.72 g (0.314 mole) of potassium hydroxide in 60 ml of water using a dropping funnel. The resulting solution was heated to 30-40° C. and 6-chlorohexanol (22.54 g, 0.165 mole) was then added in about 10 min. The solution was then refluxed overnight. After cooling 70 ml of water were added to the solid reaction mixture, and the ethanol was removed using a rotary evaporator. The residue was cooled in an ice/water bath and 70 ml of conc. hydrochloric acid were added while stirring. The solid was collected and washed with water. Then the solid was stirred at 50° C. with 250 ml of acetone. After drying at 100° C. in vacuo 24.5 g (62%) of the product was obtained.

B: 4-(6-acryloyloxyhexyloxy)cinnamic acid (13).

A mixture of 21.15 g (0.08 mole) 4-(6-hydroxyhexyloxy) cinnamic acid (13), 11.63 g (0.096 mole) N,N-dimethylaniline 8.69 g (0.096 mole) acryloyl chloride, 0.05 g of 2,6-di-t-butyl-4-methylphenol and 60 ml of 1,4-dioxane was heated at 60° C. under nitrogen atmosphere. After 2 h heating at 60° C. the mixture was filtered and dropped into a mixture of 1000 ml of water, 400 g of ice and 10 ml of 2.4 N hydrochloric acid while stirring. The solid precipitate was filtered off and recrystallized from 350 ml of ethanol. The solid was dried in a desiccator over silica gel. Yield: 19.7 g (77.3%).

EXAMPLE 8
Synthesis of (R)-4-(4-(6-Acryloyloxyhexyloxy)benzoyloxy)cinnamic acid 2-(4-(6-acryloyloxyhexyloxy)benzoyloxy)-2-phenyl-ethyl ester (18)
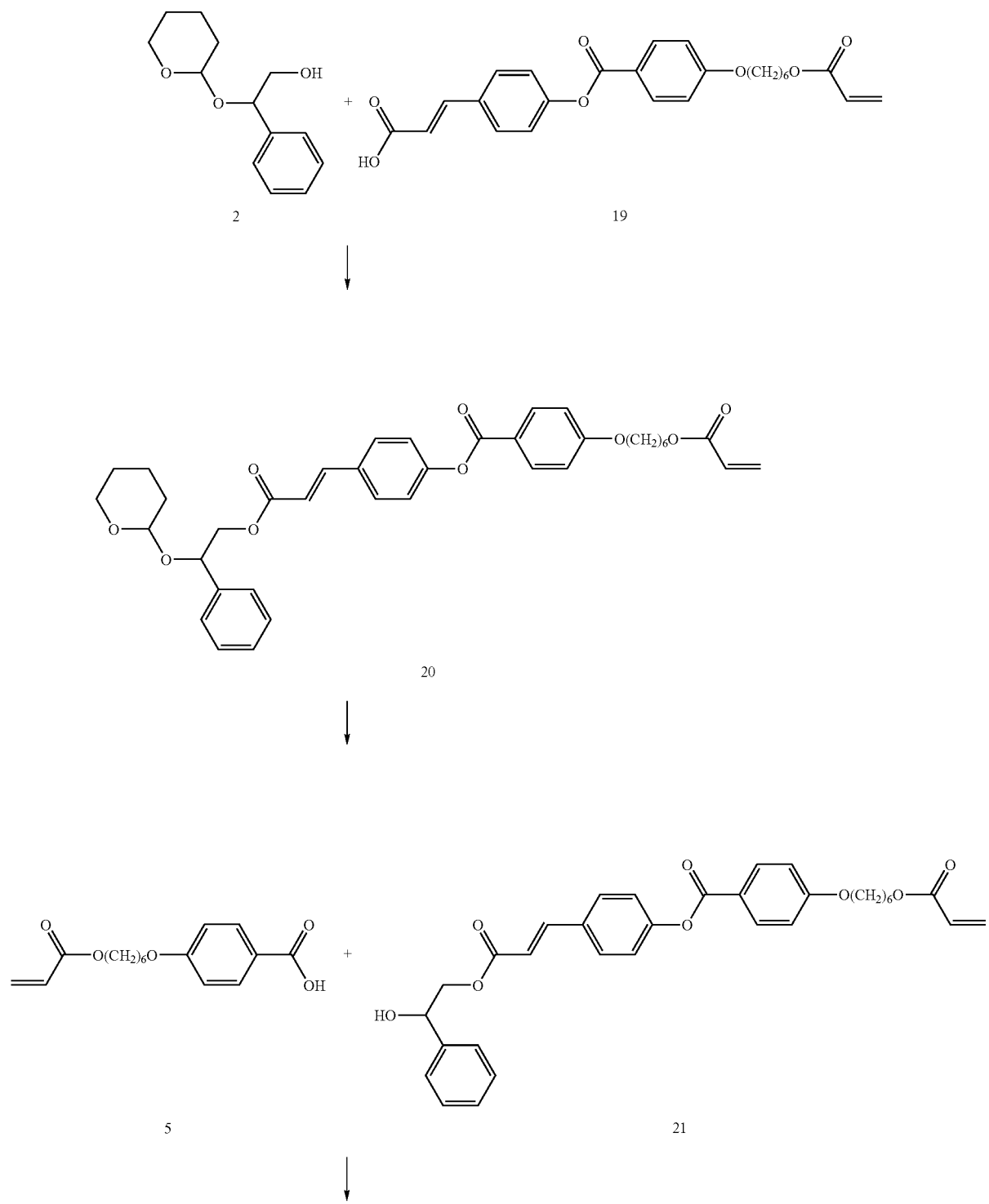

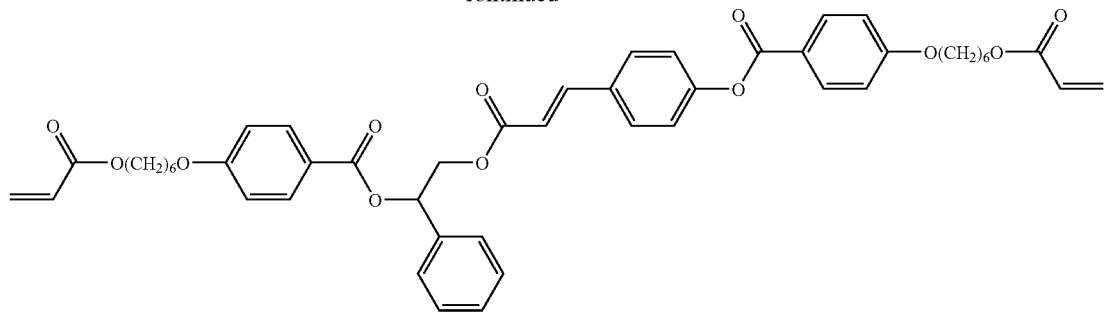

18

A: (R)-4-(4-(6-Acryloyloxyhexyloxy)benzoyloxy)cinnamic acid 2-(tetrahydropyran-2-yloxy)-2-phenyl-ethyl ester (20).

To a solution of 2.2 g (10 mmole) of (R)-2-Phenyl-2-(tetrahydro-pyran-2-yloxy)-ethanol (2) in 40 ml of dichloromethane were added 4.4 g (10 mmole) of 4-(4-(6-acryloyloxyhexyloxy)benzoyloxy)cinnamic acid (19) and 0.12 g (1 mmole) of 4-N,N-dimethylaminopyridine. The mixture was cooled in an ice-water bath. After few minutes were added 2 g (10 mmole) of N,N-dicyclohexyl carbodiimide. Then the ice-water bath was removed. The mixture was stirred at room temperature for two days. Then it was filtered through a silica pad and the solvent was evaporated at 40° C. 6.36 g of a white solid (99%) were obtained.

B: (R)-4-(4-(6-Acryloyloxyhexyloxy)benzoyloxy)cinnamic acid 2-hydroxy-2-phenyl-ethyl ester (21).

6.4 g of (R)-4-(4-(6-Acryloyloxyhexyloxy)benzoyloxy)cinnamic acid 2-(tetrahydropyran-2-yloxy)-2-phenyl-ethyl ester (20) (9.8 mmole) were dissolved in 35 ml of absolute ethanol and 0.5 g (2 mmole) of pyridinium 4-toluensulfonate and 40 mg of 4-methoxyphenol (to avoid polymerization) were added. The mixture was heated at 55° C. for 20 h. After cooling to room temperature, a white powder precipitated. It was filtered and washed with ethanol. It was dried in a dessicator with silica. 3 g of a white solid (55%) were obtained.

C: (R)-4-(4-(6-Acryloyloxyhexyloxy)benzoyloxy)cinnamic acid 2-(4-(6-acryloyloxyhexyloxy)benzoyloxy)-2-phenyl-ethyl ester (18).

0.56 g (2.7 mmole) of N,N-dicyclohexyl carbodiimide were added to a solution of 1.5 g (2.7 mmole) of (R)-4-(4-(6-acryloyloxyhexyloxy)benzoyloxy)cinnamic acid 2-hydroxy-2-phenyl-ethyl ester (21), 0.8 g (2.7 mmole) of 4-(6-acryloyloxy-hexyloxy)-benzoic acid (5) and 0.03 g (0.27 mmole) of 4-N,N-dimethylaminopyridine in 20 ml of dichloromethane, and cooled in an ice-water bath. After 3 h the ice-water bath was removed. The mixture was stirred at room temperature for two days. Then the mixture was filtered through a silica pad and the solvent was evaporated. After crystallization from ethanol, 1.2 g of the product (53%) were obtained with mp 97° C.

EXAMPLE 9

Synthesis of (R)-4-(4-(6-Acryloyloxyhexyloxy)benzoyloxy)cinnamic acid 2-(4-(6-acryloyloxyhexyloxy)benzoyloxy)-1-phenyl-ethyl ester (22)

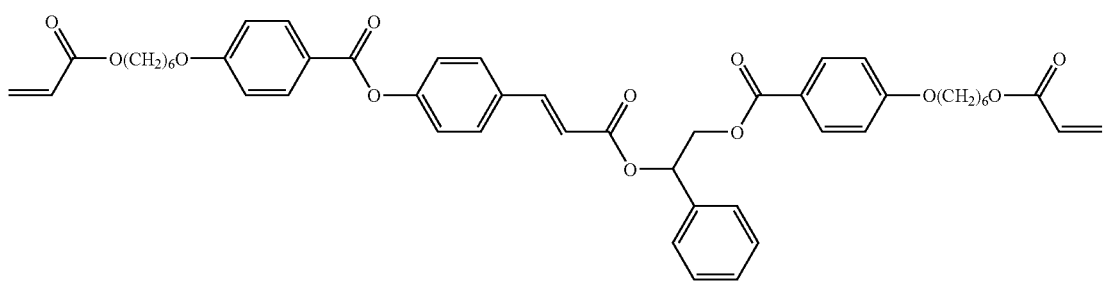

22

This compound was prepared in the same way as (R)-4-(4-(6-acryloyloxyhexyloxy)benzoyloxy)cinnamic acid 2-(4-(6-acryloyloxyhexyloxy)benzoyloxy)-2-phenyl-ethyl ester (18). In this reaction sequence compound 19 was changed for 5. mp 80° C.

EXAMPLE 10

Synthesis of 4-(4-(6-acryloyloxyhexyloxy)benzoyloxy)cinnamic acid (19)

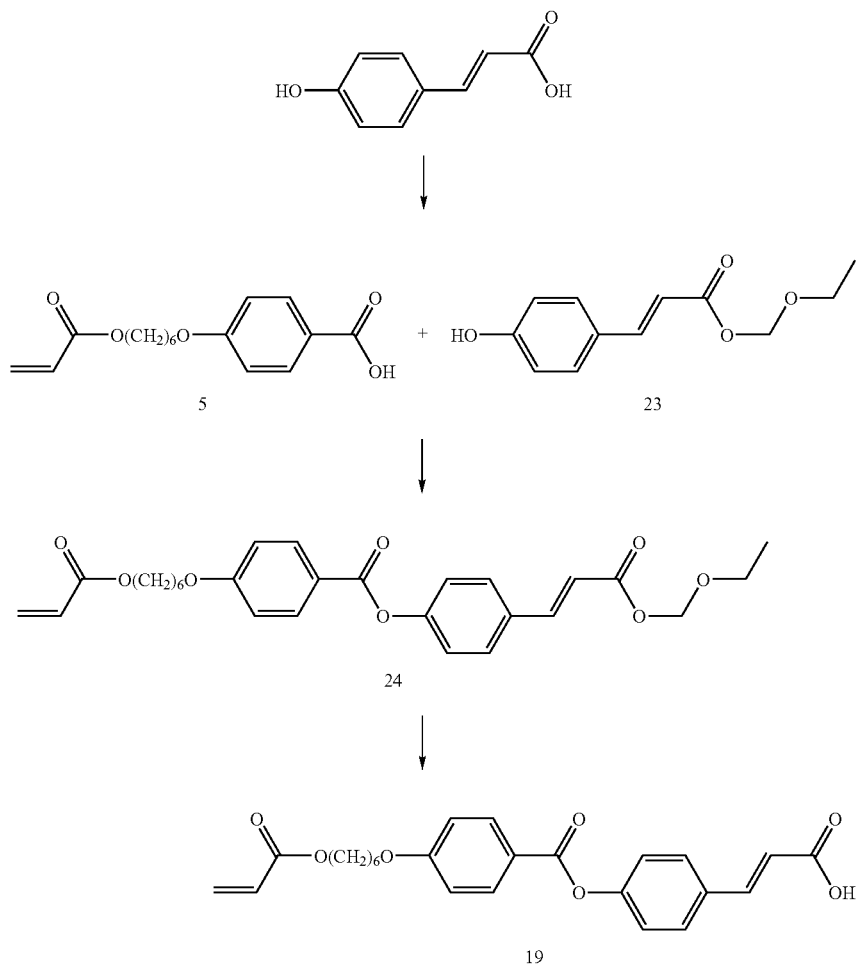

A: 4-Hydroxy-cinnamic acid ethoxymethyl ester (23).

To a solution of 16 g (100 mmole) of 4-hydroxycinnamic acid in 80 ml of dichloromethane were added 14 ml (100 mmole) of triethylamine under an $N_2$ atmosphere. The mixture was cooled in an ice-water bath, and then, 9.3 ml (100 mmole) of chloromethyl ethyl ether in 40 ml of dichloromethane were added dropwise. After stirring overnight, the solution was extracted once with 60 ml of water and once with a solution of 60 ml 0.1 M hydrochloric acid. Finally, the solution was extracted with 60 ml of saturated solution of $NaHCO_3$ and dried over $MgSO_4$. The solvent was evaporated and 18.7 g of a clear oil were obtained (purity: 90% and yield: 84%).

B: Ethoxymethyl 4-(4-(6-acryloyloxyhexyloxy)benzoyloxy)cinnamate (24).

15.7 g (0.076 mole) of N,N-dicyclohexyl carbodiimide were added to a solution of 18.7 g (0.076 mole) of 4-hydroxycinnamic acid ethoxymethyl ester (23) (90% pure), 22.2 g (0.076 mole) of 4-(6-acryloyloxy-hexyloxy)-benzoic acid (5) and 0.93 g (0.0076 mole) of 4-N,N-dimethylaminopyridine in 200 ml of dichloromethane, cooled in an ice-water bath. After two hours the ice-water bath was removed. The mixture was stirred at room temperature overnight. Then it was filtered through a silica pad and the solvent was evaporated. 15 g of the product (40%) were obtained after crystallization from ethanol.

C: 4-(4-(6-Acryloyloxyhexyloxy)benzoyloxy)cinnamic acid (19).

14.9 g of ethoxymethyl 4-(4-(6-acryloyloxyhexyloxy)benzoyloxy)cinnamate (24) (30 mmole) were dissolved in 60 ml of absolute ethanol and 0.75 g (3 mmole) of pyridinium 4-toluenesulfonate and minor amounts of 4-methoxyphenol (to avoid the polymerization) were added. The mixture was heated at 60° C. (bath temperature) for 13 h. After cooling to room temperature, a white solid appeared. It was filtered, washed with ethanol and dried in a dessicator with silica overnight. 12.7 g of a white solid were obtained (yield: 97%).

EXAMPLE 11

Synthesis of (R)-4-(6-Acryloyloxyhexyloxy)cinnamic acid 2-(4-(6-acryloyloxyhexyloxy)cinnamoyloxy)-1-phenyl-ethyl ester (25)

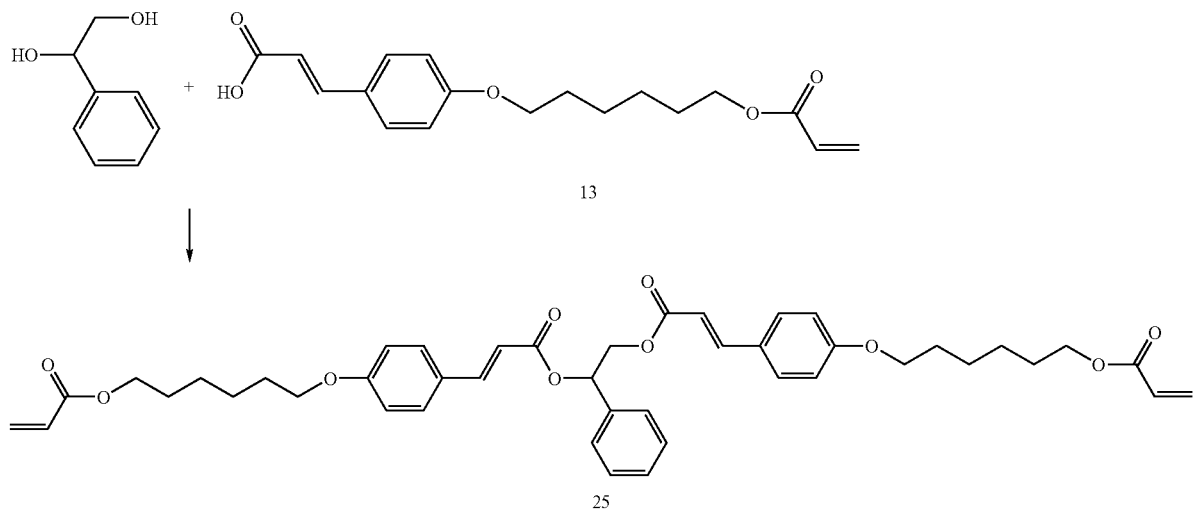

3 g (14.5 mmole) of N,N'-dicyclohexyl carbodiimide were added to a mixture of 1 g (7.25 mmole) of R-(−)-1-phenyl-1,2-ethanediol, 4.6 g (14.5 mmole) of 4-(6-acryloyloxyhexyloxy)cinnamic acid (13), 0.18 g (1.45 mmole) of 4-N,N-dimethylaminopyridine and 40 ml of dichloromethane, cooled in an ice-water bath. The mixture was stirred at room temperature for two days. After filtration, the solvent was evaporated. 3.84 g of the product (72%) were obtained as a viscous oil after elution with dichloromethane/ethyl acetate: 98/2 over silica.

EXAMPLE 12

On a clean glass surface polyimide was applied by spin-coating, followed by baking and rubbing. A homogeneous mixture of 0.156 g of compound 25
0.667 g of acrylate I
0.167 g of acrylate II
0.01 g of Darocur® 4265 (ex Ciba Geigy)

in 1.00 g of xylene containing 100 ppm of 4-methoxyphenol as inhibitor, was filtered and spin-coated with a Convac spin-coater for 30 sec at 1500 rpm on the polyimide surface. After color formation by UV irradiation at 365 nm through a photo mask in air, the film was photopolymerized under nitrogen by irradiation at 405 nm for 10 min. The CCF was obtained after 90 min postcuring at 150° C.

The chemical structures of the acrylates I and II are:

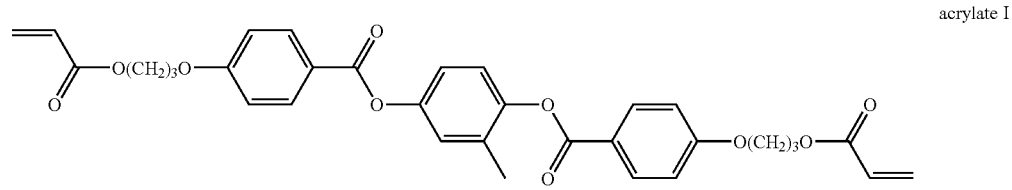

acrylate I

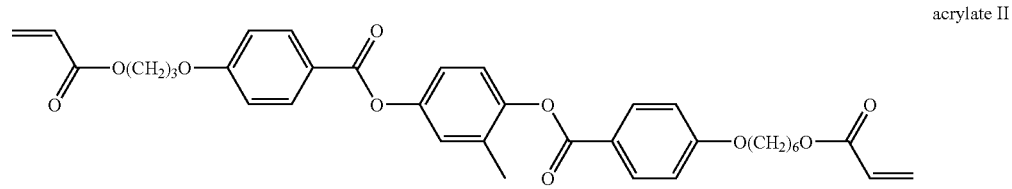

acrylate II

EXAMPLE 13

In a manner analogous to that of Example 12 a color filter was made with a mixture of
0.053 g of compound 25
0.067 g of isosorbide derivative I
0.696 g of acrylate I
0.174 g of acrylate II
0.01 g of Darocur® 4265 (ex Ciba Geigy)
in 1.00 g of xylene containing 100 ppm of 4-methoxyphenol as inhibitor. The helical twisting power of the isosorbide derivative I is opposite relative to compound 25. The concentrations of the chiral dopants were chosen such that the color filter reflects at 650 nm (red) before isomerisation and at 450 nm (blue) after isomerisation. The chemical structure of isosorbide derivative I is:

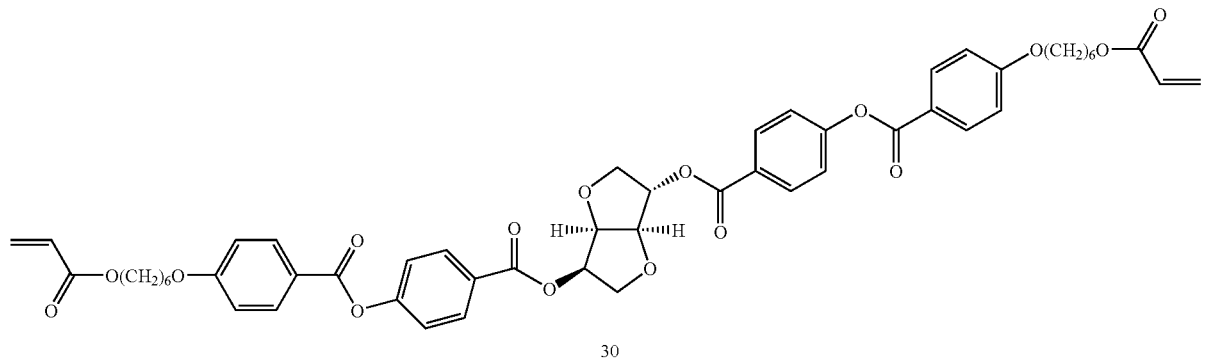

Isosorbide Derivative I

EXAMPLE 14

In a manner analogous to that of Example 12 a color filter was made with a mixture of
0.19 g of compound 18
0.64 g of acrylate I
0.16 g of acrylate II
0.01 g of Darocur® 4265 (ex Ciba Geigy)
in 1.00 g of xylene containing 100 ppm of 4-methoxyphenol as inhibitor.

EXAMPLE 15 (COMPARATIVE)

Example 12 was repeated with a mixture of
0.14 g of menthone derivative of WO 98/00428 (compound of FIG. 2B)
0.68 g of acrylate I
0.17 g of acrylate II
0.01 g of Darocur® 4265 (ex Ciba Geigy)
Instead of the Mixture of Example 13.

Figure 1B:
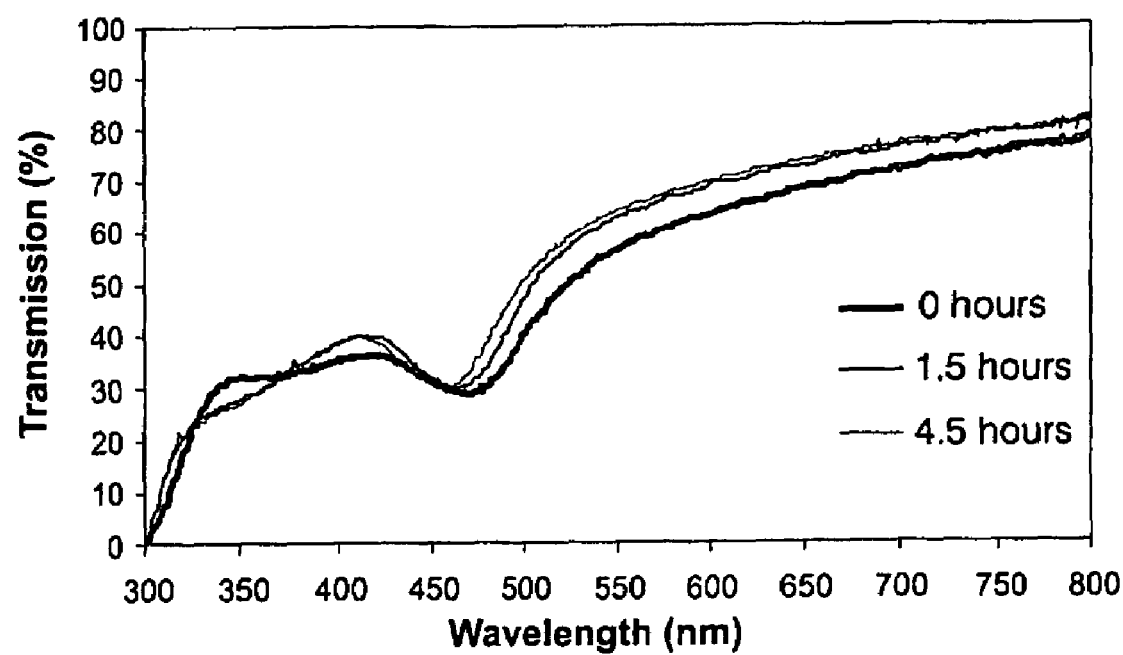

The spectra of FIGS. 1A and B show the improvements obtained with the new phenylethandiol dopant. FIG. 1A shows the transmission spectra of the CCF of Example 12 (according to the invention) before heating and after heating at 200° C. in air for the indicated times. FIG. 1B shows the transmission spectra of the CCF of Example 15 (comparative example) before heating and after heating at 200° C. in air for the indicated times. In both cases the reflection band, i.e. the minimum of transmission, is positioned around 450 nm, i.e. in other words both layers reflect blue light. In FIG. 1A the intensity of the reflection band is large (minimum transmission 5%), and the transmission in wavelength regions other than the reflection band is high (80-90%). This demonstrates the good alignment of the molecules, resulting in a nearly perfect helical structure. In FIG. 1B the intensity of the reflection band is small (minimum transmission 30%), and the transmission in wavelength regions other than the reflection band is low (~80% at long wavelength declining to ~30% at short wavelength). This demonstrates the bad alignment of the molecules, which results in an imperfect helical structure.

Upon heating at 200° C., the reflection band in FIG. 1B shifts significantly to the left (~4% after 5 hours), whereas the reflection band in FIG. 1A does not shift at all. Moreover, the intensity of the reflection band in FIG. 1B decreases upon heating, whereas the intensity of the reflection band in FIG. 1A does not. Hence, the thermal stability of the CCF with the phenylethanediol derivative as dopant is clearly better than that of the CCF with the menthone derivative as dopant.

The above results are obtained for a blue reflecting layer. For CCF's reflecting other colors the results are similar.

The spectra of example 14 show results similar to those of example 12 (FIG. 1A).

The invention claimed is:

1. A phenylethanediol derivative, characterized in that the phenylethanediol derivative comprises at least one photoconvertible group suitable for adjusting the helical twisting power of the phenylethanediol derivative, wherein the phenylethanediol has the formula

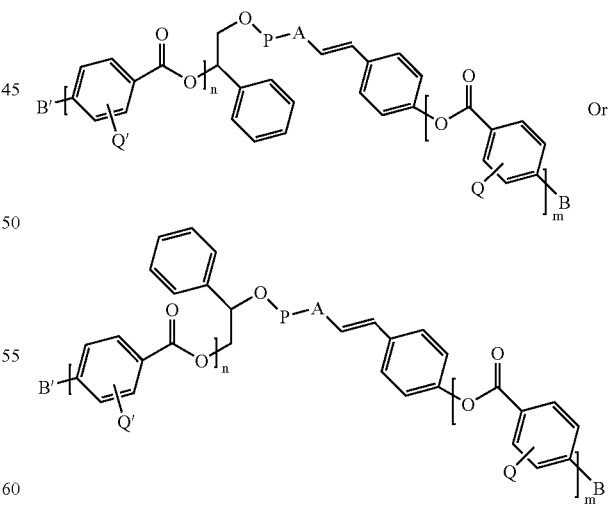

wherein
A stands for a bond or a p-phenylene group;
B and B' are independently $(O)_p-C_oH_{2o}-O-CO-CR'=CH_2$, o being 2-12, p being 0 or 1, and R' being H or $CH_3$;
P stands for a $CH_2$ or a C=O group;

Q and Q' are independently selected from H, C1-C3 alkyl, C1-C3 alkoxy, halogen, and CN;
n is an integer from 1 to 3; and
m is an integer from 0 to 2.

2. A phenylethanediol derivative, characterized in that the phenylethanediol derivative comprises at least one photo-convertible group suitable for adjusting the helical twisting power of the phenylethanediol derivative, wherein the phenylethanediol has the formula

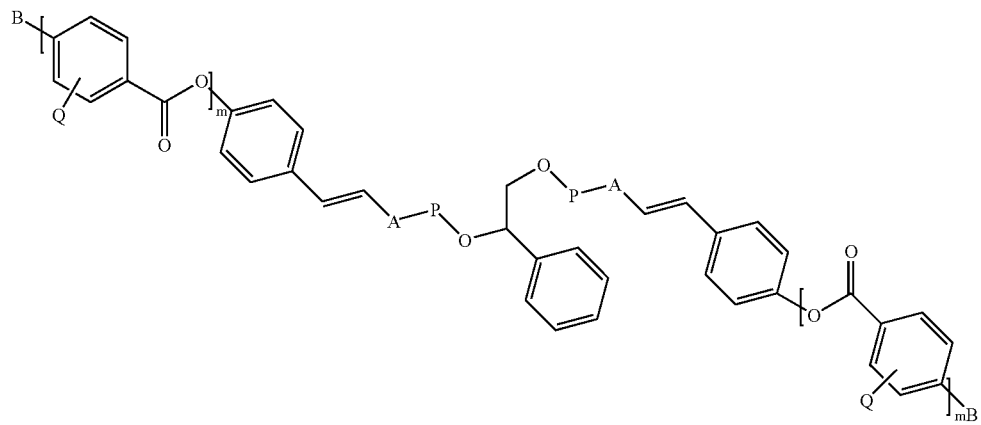

wherein
A stands for a bond or a p-phenylene group;
B is $(O)_p$—$C_oH_{2o}$—O—CO—CR'=CH$_2$, o being 2-12, p is 1, and R' being H or CH$_3$;
P stands for a CH$_2$ or a C=O group;
Q is selected from H, C1-C3 alkyl, C1-C3 alkoxy, halogen, and CN; and
m is an integer from 0 to 2.

3. A method for the preparation of the phenylethanediol derivative of claim 1 by the steps of a) synthesizing a 2-hydroxy ether-protected phenylethanediol, b) followed by etherification or esterification of the 1-hydroxy group of the 2-hydroxy ether-protected phenylethanediol with an alcohol (or derivative thereof) or acid, respectively, optionally comprising polymerizable and/or photo-convertible groups, c) then cleaving the ether-protective group to obtain a phenylethanediol derivative with a free 2-hydroxy group, and optionally d) esterification of the free 2-hydroxy group with an acid which optionally comprises one or more polymerizable and/or photo-convertible groups.

4. A cholesteric composition comprising the phenylethanediol derivative of claim 1.

5. An optical element comprising the phenylethanediol derivative of claim 1.

6. An optical color filter comprising the phenylethanediol derivative of claim 1.

7. A cholesteric composition comprising the phenylethanediol derivative of claim 2.

8. An optical element comprising the phenylethanediol derivative of claim 2.

9. An optical color filter comprising the phenylethanediol derivative of claim 2.

* * * * *